(12) United States Patent
Luo et al.

(10) Patent No.: US 7,525,015 B2
(45) Date of Patent: Apr. 28, 2009

(54) PREVENTION OF TRANSGENE ESCAPE IN GENETICALLY MODIFIED PERENNIALS

(75) Inventors: Hong Luo, Clemson, SC (US); Qian Hu, Clemson, SC (US); Kimberly Nelson Vasilchik, Griswold, CT (US); John P. Longo, South Kingston, RI (US); Albert P. Kausch, Stonington, CT (US); Barbara Zilinskas, Princeton Junction, NJ (US); Subha Lakkaraju, East Brunswick, NJ (US)

(73) Assignees: HybriGene, Inc., Hubbard, OR (US); Rutgers, The State University of New Jersey, New Brunswick, NJ (US)

(*) Notice: Subject to any disclaimer, the term of this patent is extended or adjusted under 35 U.S.C. 154(b) by 377 days.

(21) Appl. No.: 10/361,160

(22) Filed: Feb. 7, 2003

(65) Prior Publication Data

US 2003/0188341 A1 Oct. 2, 2003

Related U.S. Application Data

(60) Provisional application No. 60/355,191, filed on Feb. 7, 2002, provisional application No. 60/354,719, filed on Feb. 7, 2002, provisional application No. 60/354,772, filed on Feb. 7, 2002.

(51) Int. Cl.
C12N 15/82 (2006.01)
C12N 15/84 (2006.01)
A01H 5/00 (2006.01)
A01H 5/10 (2006.01)
C12N 15/31 (2006.01)

(52) U.S. Cl. ............... 800/287; 800/271; 800/274; 800/286; 800/288; 800/294; 800/303; 800/320; 800/323; 435/199; 435/430.1

(58) Field of Classification Search ............... 800/271, 800/274, 287, 288, 320, 323, 286, 289, 300, 800/301; 435/199
See application file for complete search history.

(56) References Cited

U.S. PATENT DOCUMENTS

| 5,470,359 | A | | 11/1995 | Huffman | |
|---|---|---|---|---|---|
| 5,639,948 | A | | 6/1997 | Michiels et al. | |
| 5,723,763 | A | * | 3/1998 | Mariani et al. | 800/306 |
| 5,723,765 | A | | 3/1998 | Oliver et al. | |
| 5,728,558 | A | * | 3/1998 | Fabijanski et al. | 800/267 |
| 5,750,867 | A | | 5/1998 | Williams et al. | |
| 5,977,433 | A | | 11/1999 | Williams et al. | |
| 6,025,546 | A | | 2/2000 | Michiels et al. | |
| 6,046,382 | A | * | 4/2000 | Mariani et al. | 800/274 |
| 6,320,097 | B1 | | 11/2001 | Mariani et al. | |
| 6,344,598 | B1 | | 2/2002 | Mariani et al. | |
| 6,372,967 | B1 | | 4/2002 | Mariani et al. | |
| 6,627,799 | B1 | | 9/2003 | Mariani et al. | |
| 6,791,011 | B1 | | 9/2004 | Paul et al. | |
| 6,833,494 | B1 | | 12/2004 | Pental et al. | |

FOREIGN PATENT DOCUMENTS

| WO | WO 98/13503 | | 4/1998 |
|---|---|---|---|
| WO | WO 00/04133 | * | 1/2000 |
| WO | WO 01/64926 | | 9/2001 |

OTHER PUBLICATIONS

McCown et al. Plant Cell Reports 9(10): 590-594 (1991).*
Pulaski, A. The Oregonian, "Monsanto's Frankengrass Sows Controversy", online article. (Sep. 12, 2004).*
Culp, C. Say No to GMOs! online newsletter, "EPA Finds Contamination From GE Turf Grass Miles From Source", (Sep. 20, 2004).*
Pollack, A. Say No to GMOS! online newsletter, "Genes From Engineered Grass Spread for Miles, Study Finds". (Sep. 20, 2004).*
Ainley, W.M. and Key, J.L. (1990) Development of a heat-shock inducible expression cassette for plants: characterization of parameters for its use in transient expression assays. Plant Mol. Biol. 14, 949-967.
Albert, H., Dale E.C., Lee E. and Ow D.W. (1995) Site-specific integration of DNA into wild-type and mutant lox sites placed in the plant genome. Plant J., 7, 649-659.
Austin, S., Ziese, M. and Sternberg, N. (1981) A novel role for site-specific recombination in maintenance of bacterial replicons. Cell, 25, 729-736.
Aoyoma, T. and Chua, N.-H. (1997) A glucocorticoid-mediated transcriptional induction system in transgenic plants. Plant J. 11, 605-612.
Bar, M., Leshem, B., Gilboa, N. and Gidoni, D. (1996) Visual characterization of recombination at FRT-gusA loci in transgenic tobacco mediated by constitutive expression of the native FLP recombinase. Theor. Appl. Genet. 93, 407-413.
Bayley, C.C., Morgan, M., Dale, E.C. and Ow, D.W. (1992) Exchange of gene activity in transgenic plants catalyzed by the Cre-lox site-specific recombination system. Plant Mol. Biol. 18, 353-361.
Broach, J.R., Guarascio, V.R. and Jayaram, M. (1982) Recombination within the yeast plasmid 2 micron circle is site specific. Cell, 29, 227-234.
Caddick, M.X., Greenland, A.J., Jepson, I., Krause, K.-P., Qu, N., Riddell, K.V., Salter, M.G., Schuch, W., Sonnewald, U. and Tomsett, A.B. (1998) An ethanol inducible gene switch for plants used to manipulate carbon metabolism. Nature Biotech. 16, 177-180.
Christensen, A.H. and Quail, P.H. (1996) Ubiquitin promoter-based vectors for high-level expression of selectable and/or screenable marker genes in monocotyledonous plants. Transgenenic Res. 5, 213-218.

(Continued)

Primary Examiner—David T Fox
(74) Attorney, Agent, or Firm—Klarquist Sparkman, LLP

(57) ABSTRACT

Genes can be introduced into plants that confer desirable traits such as, drought and stress tolerance, insect and pest resistance, as well as environmental qualities such as phytoremediation. However, possibility for transgene escape to wild and non-transformed species raises commercial and ecological concerns. Disclosed herein are methods and compositions for generating sterile plants for the prevention of transgene escape.

24 Claims, 5 Drawing Sheets
(1 of 5 Drawing Sheet(s) Filed in Color)

OTHER PUBLICATIONS

Dale, E.C. and Ow, D.W. (1991) Gene transfer with subsequent removal of the selection gene from the host genome, *Proc. Natl. Acad. Sci. USA*, 88, 10558-10562.

Gatz, C. (1997) Chemical control of gene expression. *Annu. Rev. Plant Physiol. Plant Mol. Biol*, 48, 89-108.

Gatz, C. and Lenk I. (1998) Promoters that respond to chemical inducers. *Trends Plant Sci.* 3, 322-328.

Jefferson, R.A., et al. (1987) GUS fusions: β-glucuronidase as a sensitive and versatile gene fusion marker in higher plants. *EMBO J.*, 6, 3901-3907.

Kilby, N.J., Davies, G.J., Snaith, M.R. and Murray, J.A.H. (1995) FLP recombinase in transgenic plants: constitutive activity in stably transformed tobacco and generation of marked cell clones in *Arabidopsis. Plant J.* 8, 637-652.

Komari, T., Hiei, Y., Saito, Y., Murai, N. and Kumashiro, T. (1996) Vectors carrying two separate T-DNAs for co-transformation of higher plants mediated by *Agrobacterium tumefaciens* and segregation of transformants free from selection markers. *Plant J.* 10, 165-174.

Kyozuka, J., McElroy, D., Hayakawa, T., Xie, Y., Wu, R. and Shimamoto, K. (1993) Light-regulated and cell-specific expression of tomato *rbcS-gusA* and rice *rbcS-gusA* fusion genes in transgenic rice. *Plant Physiol.* 102, 991-1000.

Lloyd, A.M. and Davis, R.W. (1994) Functional expression of the yeast FLP/*FRT* site-specific recombination system in *Nicotiana. tabacum. Mol. Gen. Genet.* 242, 653-657.

Luo, H., Lyznik, L. A., Gidoni, D. and Hodges, T. K. (2000) FLP-mediated recombination for use in hybrid plant production. *Plant. J.* 23, 423-430.

Luo, H., Van Coppenolle, B., Seguin, M. and Boutry, M. (1995) Mitochondrial DNA polymorphism and phylogenetic relationship in *Hevea brasiliensis. Mol. Breed.* 1, 51-63.

Lyznik, L.A., Hirayama, L., Rao, K.V., Abad, A. and Hodges, T.K. (1995) Heat-inducible expression of *FLP* gene in maize cells. *Plant. J.* 8, 177-186.

Lyznik, L.A., Mitchell, J.C., Hirayama, L. and Hodges, T.K. (1993) Activity of yeast FLP recombinase in maize and rice protoplasts. *Nucleic. Acids Res.* 21, 969-975.

Lyznik, L.A., Rao, K.V. and Hodges, T.K. (1996) FLP-mediated recombination of *FRT* sites in the Maize genome. *Nucleic. Acids Res.* 24, 3784-3789.

Mett, V.L., Lochhead, L.P. and Reynolds, P.H.S. (1993) Copper-controllable gene expression system for whole plants. *Proc. Natl. Acad. Sci. USA*, 90, 4567-4571.

Odell, J., Caimi, P., Sauer, B. and Russell, S. (1990) Site directed recombination in the genome of transgenic tobacco. *Mol. Gen. Genet.* 223, 369-378.

Osborne, B.I., Wirtz, U. and Baker B. (1995) A system for insertional mutagenesis and chromosomal rearrangement using the Ds transposon and Cre-*lox. Plant J.*, 7, 687-701.

Ow, D.W. (1996) Recombinase-directed chromosome engineering in plants. *Curr. Opin. Biotechnol.* 7, 181-186.

Ow, D.W. and Medberry, S.L. (1995) Genome manipulation through site-specific recombination. *Crit. Rev. Plant Sci.* 14, 239-261.

Pickett, J.A. and Poppy, G.M (2001) Switching on plant genes by external chemical signals. *Trends Plant Sci.* 6, 137-139.

Qin, M., Bayley, C., Stockton, T. and Ow, D.W. (1994) Cre recombinase-mediated site-specific recombination between plant chromosomes. *Proc. Natl. Acad. Sci. USA*, 91, 1706-1710.

Russell, S.H., Hoopes, J.L. and Odell, J.T. (1992) Directed excision of a transgene from the plant genome. *Mol. Gen. Genet.* 234, 49-59.

Sonti, R.V., Tissier, A.F., Wong, D., Viret, J.-F. and Signer, E.R. (1995) Activity of the yeast FLP recombinase in *Arabidopsis. Plant Mol. Biol.* 28, 1127-1132.

Srivastava, V., Anderson, O.D. and Ow, D.W. (1999) Single-copy transgenic wheat generated through the resolution of complex integration patterns. *Proc. Natl. Acad. Sci. USA*, 96, 11117-11121.

Stuurman, J., de Vroomen, M.J., Nijkamp, H.J.J. and van Haaren, M.J.J. (1996) Single-site manipulation of tomato chromosomes in vitro and in vivo using Cre-*lox* site-specific recombination. *Plant Mol. Biol.* 32, 901-913.

Vergunst, A.C. and Hooykaas, P.J.J. (1998) Cre/*lox*-mediated site-specific integration of *Agrobactetium* T-DNA in *Arabidopsis thaliana* by transient expression of *cre. Plant Mol. Biol.* 38, 393-406.

Vergunst, A.C., Jansen, L.E.T and Hooykaas, P.J.J. (1998) Site-specific integration of *Agrobacterium* T-DNA in *Arabidopsis thaliana* mediated by Cre recombinase. *Nucl. Acids Res.* 26, 2729-2734.

Ward, E.R., Ryals, J.A. and Miflin, B.J. (1993) Chemical regulation of transgene expression in plants. *Plant Mol. Biol.* 22, 361-366.

Zuo, J. Niu, Q-W, and Chua N.-H. (2000) An estrogen receptor-based transactivator XVE mediates highly inducible gene expression in transgenic plants. *Plant J.* 24, 265-273.

Zuo, J. Niu, Q.-W., Møller, S. G. and Chua N.-H. (2001) Chemical-regulated, site-specific DNA excision in transgenic plants. *Nat. Biotechnol.* 19, 157-161.

Mouradov et al., "Genetic Engineering of Reproductive Sterility in *pinus Radiata*," *Acta Hortic.* 461:417-423 (1998).

Luo et al., in *Molecular Breeding of Forage and Turf*, Hopkins et al. (eds.) pp. 245-254, Kluwer Academic Publishers, Dordrecht/Boston/London (2004).

De Block et al., "Engineered Fertility Control in Transgenic *Brassica napus* L.: Histochemical Analysis of Anther Development," *Planta* 189:218-225 (1993).

De Block et al., "The Development of a Nuclear Male Sterility System in Wheat. Expression of the *barnase* Gene Under the Control of Tapetum Specific Promoters," *Theor. Appl. Genet.* 95:125-131 (1997).

Mariani et al., "Induction of Male Sterility in Plants by a Chimaeric Ribonuclease Gene," *Nature* 347:737-741 (1990).

Paul et al., "The Isolation and Characterisation of the Tapetum-Specific *Arabidopsis thaliana* A9 Gene," *Plant Mol. Biol.* 19:611-622 (1992).

Luo et al., "Controlling Transgene Escape in GM Creeping Bentgrass," *Mol. Breeding* 16:185-188 (2005).

* cited by examiner

FIG. 5 Total floral infertility linked to CHEM inducibility
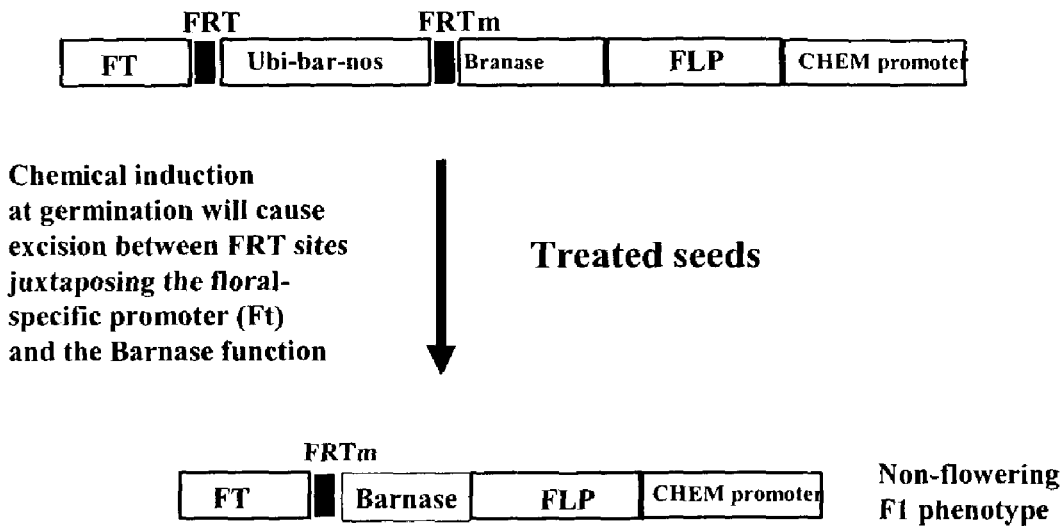
FIG. 6 Bio-herbicide linked to CHEM inducibility
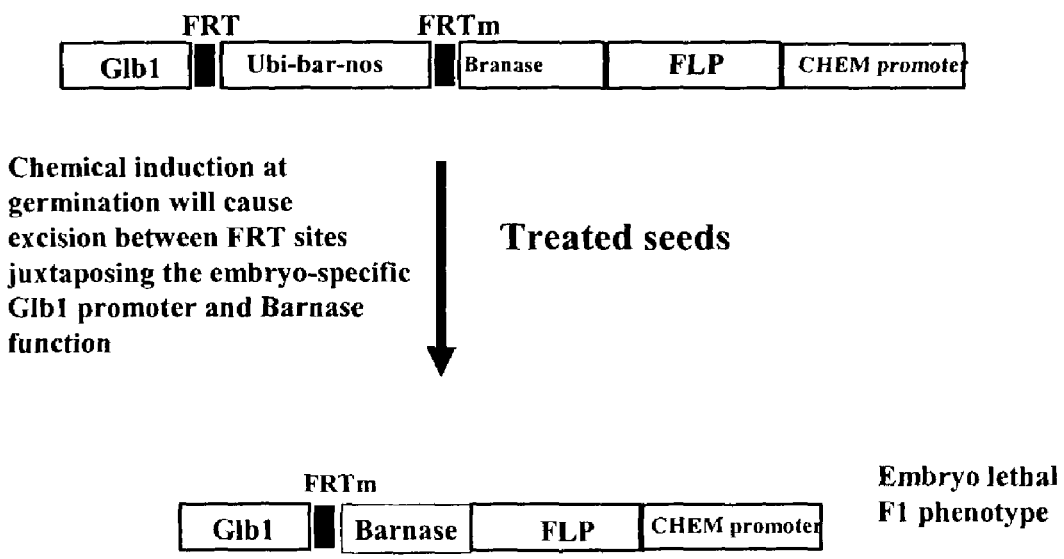

FIG. 7: Bio-herbicide crossed in with to Light induciblity
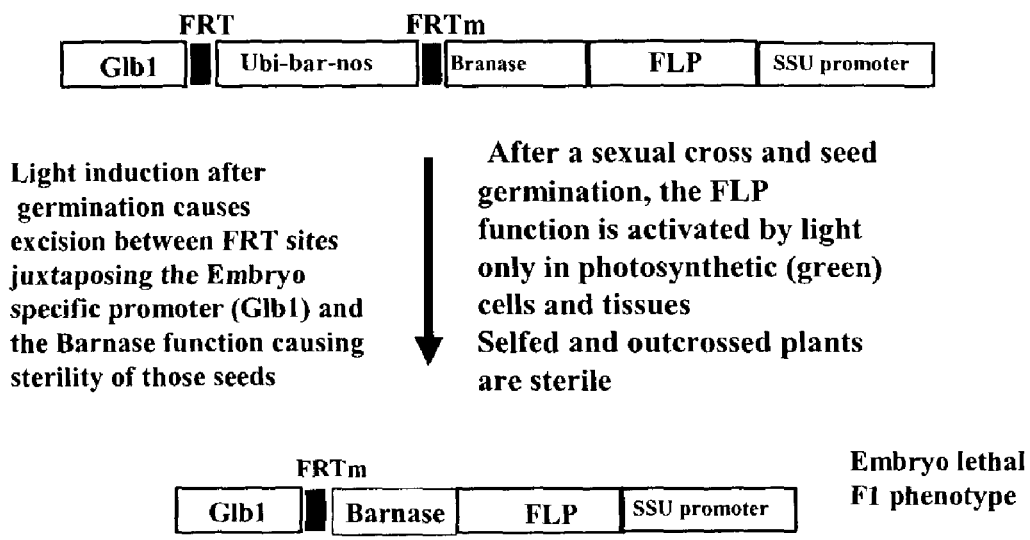
FIG. 8: F1 generation seed sterility linked to light induciblity
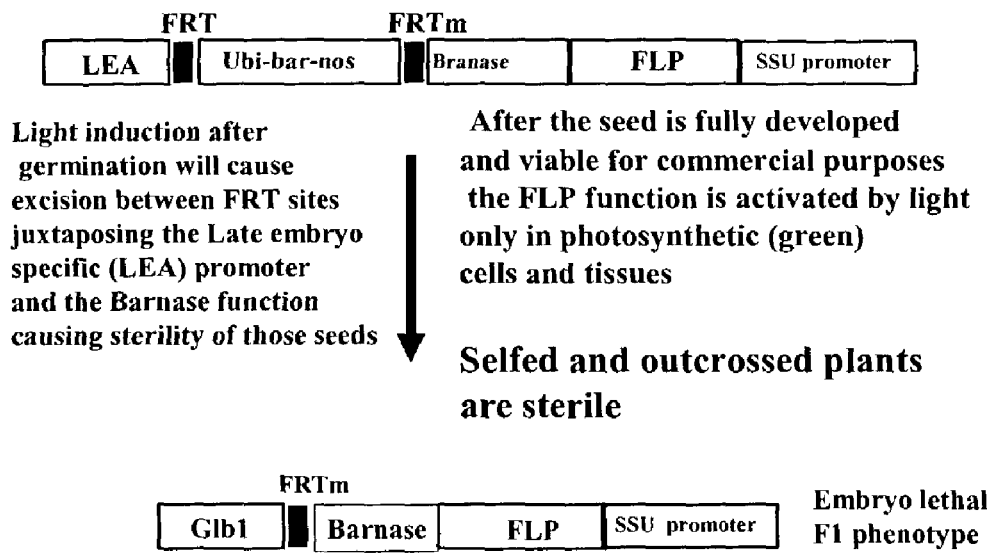

SEQUENCE LISTING

<160> NUMBER OF SEQ ID NOS: 4

<210> SEQ ID NO 1
<211> LENGTH: 220
<212> TYPE: DNA
<213> ORGANISM: Oryza sativa

<400> SEQUENCE: 1

```
atggccgccg agccgcccac cgatgacggc gcggtccggg tggcggcggg gctgacgaag      60
tgcgtgtccg ggtgcggtag caaggtgacc tcctgcttgc tcggctgcta cggcggcggc     120
ggcggcgccg ccgccgccgc gacggcgatg ccgttctgcg tcatcggctg caccagcgac     180
gtcttgtcct gcgccaccgg ctgctccacc tcgctctgat                           220
```

<210> SEQ ID NO 2
<211> LENGTH: 1340
<212> TYPE: DNA
<213> ORGANISM: Oryza sativa

<400> SEQUENCE: 2

```
gagctcaccg gcgaggcggt gcgtctcctc ggagatgtgg tagaagctgg cgccccattt      60
catggcggcg agcgggccgg gcggcctcct gccgcagcgg gattcggtgg ctagaccgat     120
ctgtgggtgg aggacgggga cgaggtagag gagacagagg cggcattgga agaggggaag     180
aggaggagga agtggtggca ggcagaggcg gatgaggaac ttgcgccagc gacgtggata     240
tggaggggc gacggcaatg gggaggcggc gatggaagcg aggagatggg caggcggcgg     300
aggcagcggt ggattttttt tttcttttc tttttcggac cctttacccct gctcggtgat     360
tcttcttttt tatacagcac gacggcttct cctattcacg acgcctcggc tggaccatgg     420
accgttggcc actggagcat tcttccatga tctagatttt ttttttcact caactttact     480
acttcacatc tgatggctgg tgttgaattc attgtgcatc caacggtcat tattaaattg     540
atgacgtggc gcaatgaggt gacgaaacac tttactttt ttactacttt agatctgtcg      600
gcaggagtcc cagatagata cttgagctgg ttagttgggt tttggatgga gtaactttct     660
gcagactgca acattctgac acacgtagca gcacaaaaga gttgcgaaca aacttggact     720
gttaacatgt caacgcataa aactgaaaaa aaaaaccctgt caaaatgcat aataaataaa    780
actgaaaaaa aataagaata aatgttgaga gtgggatttg aacccacgcc ctttcggacc     840
agaaccttaa tctggcgcct tagaccaact cggccatctc aacttttgc tctgtcatcc      900
aaacaaagtt ataagaaatc atataataat aactaagact tgatgcctca gtagtttagt     960
taaactaatt tgaatttgtt agtacagttt gcatttcaaa ttgttccaat ttggacgcca    1020
cggctggttt cagttgctca cgacgcctca cacacatatt ttgcttcctt gcttgtgaca    1080
ctagggcaca aaactccaac actcaaacga cacttcacgc atctctcctg aaatcttgca    1140
cccccccaact ctgcatcgtc gcgtataaaa tgcagaccaa accccagctc aactctgcat   1200
catcatcatc aactcgatag aaaaagaaag aaattaaaaa gaaatcacg gcgcgtgagc    1260
ttgcagagac agcaatggtg agagttgctg ccgccgcggc ggtgctcgtg ctggcggcgg    1320
cggcggcggc ggcggcggcc                                                1340
```

<210> SEQ ID NO 3
<211> LENGTH: 21
<212> TYPE: DNA
<213> ORGANISM: Artificial Sequence

```
-continued

<220> FEATURE:
<223> OTHER INFORMATION: PCR primer

<400> SEQUENCE: 3
cacaggaaac aggatccgcg g                                                    21

<210> SEQ ID NO 4
<211> LENGTH: 29
<212> TYPE: DNA
<213> ORGANISM: Artificial Sequence
<220> FEATURE:
<223> OTHER INFORMATION: PCR primer

<400> SEQUENCE: 4
cgcgagctcg ccggaaagtg aaattgacc                                            29
```

PREVENTION OF TRANSGENE ESCAPE IN GENETICALLY MODIFIED PERENNIALS

CROSS-REFERENCE TO RELATED APPLICATIONS

This application claims priority to U.S. Provisional Application Nos: 60/355,191; 60/354,719; and 60/354,772; all filed on Feb. 7, 2002, and all herein incorporated by reference.

FIELD

The present disclosure relates to plant genome modification methods that result in floral sterile phenotypes and thus decrease transgene escape.

BACKGROUND

The improvement of many plants, such as turfgrass, through conventional breeding usually relies on the identification of a single improved trait within a cultivar and is restricted to germplasm that is capable of sexual crosses to yield fertile offspring. An improved trait within a given cultivar once identified, is followed by extensive backcrossing, selection and evaluation to produce a commercially viable product. This process can require up to fifteen years, and is restricted to traits confined to the gene pool of the plant.

In contrast, many important crop plants are genetically transformed with genes from other species, even across kingdom barriers. The introduction of cloned genes into plant cells and recovery of stable fertile transgenic plants can be used to make modifications in a plant, and has created the potential for genetic engineering of plants for crop improvement. Genetic modifications by plant transformation allow stable alterations in biochemical processes that direct traits such as increased yield, disease and pest resistance, herbicide tolerance, nutritional quality, drought and stress tolerance, as well horticultural qualities such as pigmentation and growth, and other agronomic characteristics for crop improvement. In these methods, foreign DNA is introduced into the eukaryotic plant cell, followed by isolation of cells containing the foreign DNA integrated into the cell's DNA, to produce stably transformed plant cells.

One drawback that arises regarding transgenic improvement of perennials, such as turfgrass, is the possibility for transgene escape to wild and non-transformed species. For example, creeping bentgrass is an out-crossing and wind pollinated, stoloniferous, perennial species. These traits can increase the risk of outcrossing, persistence, and introgression of alien genes into an adjacent population. However, the bulk of most of the risk assessment work conducted on transgenic plants has been on annual and/or self-pollinating crops. As a result, there is a lack of information on the potential risks from the commercialization and large-scale seed production of these types of transgenic crops. In a three-year field study on gene-flow of transgenic bentgrass, it was observed that pollen from the transgenic nursery traveled at least 411.5 feet (Wipff and Friker, *Diversity* 16:36-9, 2000). Therefore, there is a need to develop methods which decrease, or even prevent transgene escape in perennial plants.

Traditionally, male sterility has been used in crop plants for the production of hybrid varieties with higher yield, increased resistance to disease, and enhanced performance in different environments compared with the parental lines. In both corn and rice, cytoplasmic male-sterile (CMS) plants were successfully used on a large scale in hybrid seed production. However, the use of a unique type of cytoplasm has drawbacks because of the increased vulnerability of the plant to insects and pathogens (Levings, *Science* 250:942-7, 1990). Therefore, alternative methods for producing hybrid plants are needed. In corn, detasseling (removal of the male part of line A) and then pollination by line B for hybrid production is an alternative, but detasseling is costly. In addition, neither detasseling nor CMS systems are available for many economically important crops, such as wheat, soybean, canola, or barley, which are still bred and grown as inbred varieties.

An alternative to CMS and detasseling is the development of male sterility by the selective ablation of tapetal cells, which are important for pollen development (Mariani et al., *Nature* 357:384-7, 1990; Moffatt and Somerville, *Plant Physiol.* 86:1150-4, 1988; Tsuchiya et al., *Plant Cell Physiol.* 36:487-94, 1995; Xu et al., *Proc. Nat. Acad. Sci. USA* 92:2106-10, 1995). Selective ablation of tapetal cells by cell-specific expression of cytotoxic molecules (Mariani et al., *Nature* 357:384-7, 1990) or an antisense gene (Xu et al., *Proc. Nat. Acad. Sci. USA* 92:2106-10, 1995) blocks pollen development, resulting in male sterility in annuals. However, methods to restore the fertility for the antisense-caused male sterility have not been developed. Luo and Hodges (*Plant J.* 23:423-430, 2000), using a site-specific recombinase eliminated, in transgenic male-sterile plants, the male-sterility causing elements integrated into the host genome by crossing with pollen from a plant expressing a recombinase, yielding hybrid seeds.

SUMMARY

The threat of transgene escape to other plants is a real concern, and control of this problem is important if transgenic perennial plants are released. Therefore, methods are needed that decrease or prevent the risk of spreading a transgene from a transgenic perennial into the environment through outcrossing. Disclosed herein are methods for generating sterile plants, such as male sterile plants, which decrease transgene escape. Sterile transgenic plants do not produce significant numbers of viable pollen grains, thus decreasing or preventing the potential risk of transgene escape into the surrounding environment by outcrossing with wild species.

Methods to generate sterile perennial plants, such as male and/or female sterile plants, are disclosed herein by functionally deleting floral structures, such as the tapetum. In one example, a cytotoxic molecule, such as a barnase gene or an anti-sense floral-specific gene, is driven by a floral-specific promoter creating defective floral structures, such as sterile pollen. For example, expression of the cytotoxin, that in one example produces a protein product that decreases the presence and/or production of tapetum, results in male sterility.

Also disclosed herein is the use of site-specific recombination to generate male and female sterile perennial plants. The seeds produced from such plants will produce sterile plants, thus decreasing or preventing transgene escape. In addition, second-generation sterile perennials will protect the proprietary lines developed by seed companies. In one example, the method includes crossing a first fertile plant having one or more desirable traits, with a second fertile plant, which can also have one or more desirable traits. For example, the first plant can be resistant to glufosinate and the second plant resistant to glyphosate. The first fertile plant contains a vector which includes a floral-specific promoter operably linked to a blocking sequence, such as a selectable marker, wherein the blocking sequence is flanked by recombining site sequences. The vector also includes a cytotoxic sequence downstream of the promoter and selectable marker, and positioned such that its expression is activated by the floral-specific promoter in the presence of a recombinase, which results in recombination at the recombining site sequences and removal of the blocking sequence. The second fertile plant includes another vector which includes a promoter, such as a constitutively active or inducible promoter, operably linked to a recombinase. If an inducible promoter is used, the second fertile plant is contacted with an inducing agent, before, during, or after crossing the first and second fertile plants. The constitutively active promoter, or inducing agent that activates the inducible promoter, permits recombinase expression. The expressed recombinase protein interacts with the recombining sites of the other vector, resulting in recombination, removal of the blocking sequence such that the floral-specific promoter is now operably linked to the cytotoxin, thereby driving expression of the cytotoxin. The resulting progeny of such a cross have a sterile phenotype.

In an alternative example, instead of using two vectors, all of the elements can be placed on a single vector, which is transfected into plants or plant cells. For example, the first or the second fertile plant contains a vector which includes a floral-specific promoter operably linked to a blocking sequence, wherein the blocking sequence is flanked by a recombining site sequence, a cytotoxic sequence downstream of the blocking sequence such that the cytotoxic sequence is operably linked to the promoter upon recombination, and a promoter (such as a constitutively active or inducible promoter) operably linked to a recombinase. If an inducible promoter is used, the plant transfected with the vector is contacted with an inducing agent, before, during, or after crossing the plants. The inducing agent, or constitutively active promoter, promotes recombinase expression. The expressed recombinase protein interacts with the recombining sites, resulting in recombination, removal of the blocking sequence such that the floral-specific promoter is now operably linked to the cytotoxin, thereby driving expression of the cytotoxin. The resulting progeny of such a cross are sterile.

Similar methods can be used to delete unwanted DNA sequences (such as antibiotic resistance markers) from transgenic plants, and to generate bioherbicides.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 is a digital image of creeping bentgrass transformed with the vector shown in FIG. 1A or 1B following exposure to herbicide.

FIGS. 5-8 are schematic diagrams of methods that can be used to generate sterile plants using a recombinase system.

SEQUENCE LISTING

Figure 1A:
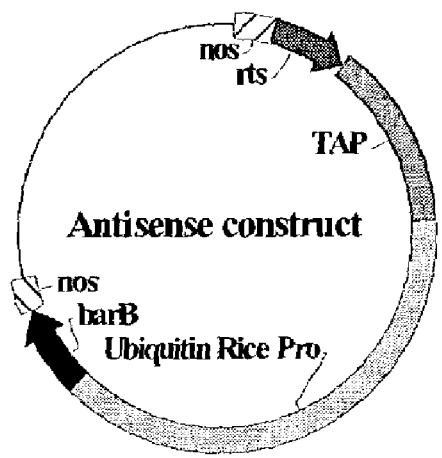
FIGS. 1A and 1B are schematic diagrams of plasmids that include (A) an antisense rts gene or (B) a barnase gene, under the control of a rice tapetum-specific promoter (TAP).

The nucleic acid sequences listed in the accompanying sequence listing are shown using standard letter abbreviations for nucleotide bases. Only one strand of each nucleic acid sequence is shown, but the complementary strand is understood as included by any reference to the displayed strand.

SEQ ID NO: 1 is a rice tapetum-specific (rts) sequence.
SEQ ID NO: 2 is a nucleic acid sequence of a rice tapetum-specific promoter.
SEQ ID NOS: 3 and 4 are primers used to obtain a barnase coding sequence.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, the singular forms "a" or "an" or "the" include plural references unless the context clearly dictates otherwise. For example, reference to "a transgenic plant" includes one or a plurality of such plants, and reference to "the tapetum-specific promoter" includes reference to one or more tapetum-specific promoters and equivalents thereof known to those skilled in the art, and so forth.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Anther-specific gene: A gene sequence that is primarily expressed in the anther, relative to expression in other plant tissues. Includes any anther-specific gene whose malfunction or functional deletion results in male-sterility. Examples include, but are not limited to: anther-specific gene from tobacco (GenBank Accession Nos. AF376772-AF376774), and Osg4B and Osg6B (GenBank Accession Nos. D21159 and D21160).

Anther-specific promoter: A DNA sequence that directs a higher level of transcription of an associated gene in anther tissue relative to the other tissues of the plant. Examples include, but are not limited to: anther-specific gene promoter from tobacco (GenBank Accession Nos. AF376772-AF376774), and the promoters of Osg4B and Osg6B (GenBank Accession Nos. D21159 and D21160).

Antisense molecules: Nucleic acid molecules that are specifically hybridizable or specifically complementary to either RNA or the plus strand of DNA (Weintraub, *Scientific American* 262:40, 1990). In a cell, the antisense nucleic acids hybridize to the corresponding mRNA, forming a double-stranded molecule. The antisense nucleic acids interfere with the translation of the mRNA, since the cell will not translate a mRNA that is double stranded. In one example, an antisense oligomer is about 15 nucleotides. The use of antisense molecules to inhibit the in vitro translation of genes is well known in the art (Marcus-Sakura, *Anal. Biochem.* 172:289, 1988).

An effective floral-specific antisense molecule, such as a tapetum-specific antisense molecule, is characterized by its ability to decrease or inhibit the expression of the floral-specific molecule. Complete inhibition is not necessary for effectiveness, some sequences are capable of inhibiting the expression of a floral-specific molecule by at least 15%, 30%, 40%, 50%, 60%, 70%, 80%, 90%, 95%, 98%, 99% or 100%. An effective antisense molecule is additionally characterized by being sufficiently complementary to a floral-specific encoding nucleic acid sequences. Sufficient complementary indicates that the effective antisense molecule can specifically disrupt the expression of a floral-specific gene, and not significantly alter the expression of genes other than a floral-specific gene.

Barnase: A cytotoxic extracellular ribonuclease. Examples of particular barnase DNA and protein sequences that can be used to practice the methods disclosed herein can be found on Genbank (for example Accession Nos: S01373, X15545 and M14442). Includes sequences obtained from *Bacillus amyloliquefaciens*, as well as other organisms, such as *Aspergillus oryzae* (RNase-T1). Includes variants of wild-type barnase sequences that retain barnase biological function, such as cytotoxic activity.

Binding/stable binding: A oligonucleotide sequence, such as an antisense sequence, binds or stably binds to a target nucleic acid if a sufficient amount of the oligonucleotide forms base pairs or is hybridized to its target nucleic acid, to permit detection of that binding. Binding can be detected by physical or functional properties of the target:oligonucleotide complex. Binding between a target and an oligonucleotide can be detected by any method known to one skilled in the art, including functional and physical binding assays. Binding can be detected functionally by determining whether binding has an observable effect upon a biosynthetic process such as expression of a gene, DNA replication, transcription and translation.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method that is widely used involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt. The binding between an oligomer and its target nucleic acid is frequently characterized by the temperature ($T_m$), at which 50% of the oligomer is melted from its target. A higher $T_m$ means a stronger or more stable complex relative to a complex with a lower $T_m$.

Blocking sequence: A DNA sequence of any length that blocks a promoter from effecting expression of a targeted gene. In one example, a vector of the present disclosure includes a floral-specific promoter operably linked to a cytotoxin, the promoter and cytotoxin being separated by a blocking sequence that is in turn bounded on either side by recombining site sequences. In the absence of the appropriate recombinase, the cytotoxin is not expressed. Presence of the appropriate recombinase effects the removal of the blocking sequence at the specific recombining site sequences, thereby directly linking the cytotoxin and the floral-specific promoter, allowing expression of the cytotoxin by the floral-specific promoter. Examples of blocking sequences include, but are not limited to non-coding DNA sequences, and selectable marker gene sequences.

Comprises: A term that means "including." For example, "comprising A or B" means including A or B, or both A and B, unless clearly indicated otherwise.

Cytotoxin: An agent, such as a protein, that can kill a cell, or decrease the ability of the cell to function as it would in the absence of the toxin. For example, expression of a cytotoxic gene, or antisense molecule, can be fatal to the cell expressing such a gene or molecule. Examples include, but are not limited to ribonuclease genes, such as barnase (from *Bacillus amylstiquefaciens*) and RNase-T1 (from *Aspergillus oryzae*) and antisense molecules that decrease or inhibit cell development or kill cells, such as molecules that interfere with tapetum development. Additional examples include avidin, auxin production-related genes, DAM methylase, and Diphtheria toxin.

Decrease in or prevention of transgene escape: A substantial reduction in the viability of pollen, which decreases the risk of a transgene in a transgenic plant escaping into another plant individual or population. Complete prevention of transgene escape is not necessary for effectiveness. In one example, a substantial reduction in pollen viability is when no more than 0.1% of the pollen produced by a plant is viable (as compared to the viability of wild-type pollen of the same variety of plant), for example, no more than about 0.01% of the pollen is viable, for example, no more than about 0.001% of the pollen is viable, or even less.

Deletion: The removal of a sequence of a nucleic acid, for example DNA, the regions on either side being joined together.

Desirable trait: A characteristic which is beneficial to a plant, such as a commercially desirable, agronomically important trait. Examples include, but are not limited to: resistance to insects and other pests and disease-causing agents (such as viral, bacterial, fungal, and nematode agents); tolerance or resistance to herbicides; enhanced stability; increased yield or shelf-life; environmental tolerances (such as tolerance to drought, heat, chilling, freezing, excessive moisture, salt stress, or oxidative stress); male sterility; and nutritional enhancements (such as starch quantity and quality; oil quantity and quality; protein quality and quantity; amino acid composition; and the like). On one example, a desirable trait is selected for through conventional breeding. In another example, a desirable trait is obtained by transfecting the plant with a transgene(s) encoding one or more genes that confer the desirable trait to the plant.

Floral-specific gene: A gene sequence that is primarily expressed in floral tissue, such as the tapetum, anther, ovule, style, or stigma, relative to the other tissues of the plant. Includes any floral-specific gene whose malfunction or functional deletion results in sterility of the plant.

Floral-specific promoter: A DNA sequence that directs a higher level of transcription of an associated gene in floral tissues relative to the other tissues of the plant. Examples include, but are not limited to: anther-specific promoters, pollen-specific promoters, tapetum-specific promoters, ovule-specific promoters, megasporocyte-specific promoters, megasporangium-specific promoters, integument-specific promoters, stigma-specific promoters, and style-specific promoters. In one example, floral-specific promoters include an embryo-specific promoter or a late embryo-specific promoter, such as the late embryo specific promoter of DNH1 or the HVA1 promoter, the GLB1 promoter from corn, and any of the Zein promoters (Z27).

The determination of whether a sequence operates to confer floral specific expression in a particular system (taking into account the plant species into which the construct is being introduced, the level of expression required, etc.), is preformed using known methods, such as operably linking the promoter to a marker gene (e.g. GUS), introducing such constructs into plants and then determining the level of expression of the marker gene in floral and other plant tissues. Sub-regions which confer only or predominantly floral expression, are considered to contain the necessary elements to confer floral specific expression.

Functional deletion: A gene is functionally deleted when the function of the gene or gene product is reduced or eliminated. For example, anti-sense molecules can be used to functionally delete a gene. In another example, a cell or tissue is functionally deleted when the function of the cell or tissue is reduced or eliminated. For example, cytotoxic genes, such as barnase, can be used to functionally delete floral-specific cells, such as the tapetum, thereby resulting in sterility of the plant.

Functionally equivalent: Nucleic acid sequence alterations in a vector that yield the same results described herein. Such sequence alterations can include, but are not limited to, conservative substitutions, deletions, mutations, frameshifts, and insertions. For example, in a nucleic acid including a barnase sequence that is cytotoxic, a functionally equivalent barnase sequence may differ from the exact barnase sequences disclosed herein, but maintains its cytotoxic activity. Methods for determining such activity are disclosed herein.

Isolated: An "isolated" biological component (such as a nucleic acid or protein) has been substantially separated, produced apart from, or purified away from other biological components in the cell of the organism in which the component naturally occurs, i.e., other chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids, proteins and peptides.

Male-sterile plant: A plant of a given plant species that contains no or little viable pollen (such as less than 0.1% viability as compared to a non-male sterile plant of the same variety) and thus is male-sterile due to expression of a male-sterility gene or gene construct(s). In one example, such plants have a decreased ability to transfer its transgene(s) to another plant.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide (such as DNA or RNA) sequence of at least 9 nucleotides, for example at least 15, 18, 24, 25, 27, 30, 50, 100 or even 200 nucleotides long.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Peptide: A chain of amino acids of which is at least 4 amino acids in length. In one example, a peptide is from about 4 to about 30 amino acids in length, for example about 8 to about 25 amino acids in length, such as from about 9 to about 15 amino acids in length, for example about 9-10 amino acids in length.

Perennial: A plant which grows to floral maturity for three seasons or more. Whereas annual plants sprout from seeds, grow, flower, set seed and senesce in one growing season, perennial plants persist for several growing seasons. The persistent seasonal flowering of perennial plants may also, but not necessarily, include light and temperature requirements that result in vernalization. Examples include, but are not limited to: certain grasses, such as turfgrass, forage grass or ornamental grasses; trees, such as fruit and nut crop trees (for example bananas and papyas), forest and ornamental trees, rubber plants, and shrubs; grapes; roses; and wild rice.

Pollen-specific gene: A DNA sequence that directs a higher level of transcription of an associated gene in microspores and/or pollen (i.e., after meiosis) relative to the other tissues of the plant. Examples include, but are not limited to: pollen-specific promoters LAT52, LAT56, and LAT59 from tomato (GenBank Accession Nos. BG642507, X56487 and X56488), rice pollen specific gene promoter PS1 (GenBank Accession No. Z16402), and pollen specific promoter from corn (GenBank Accession No. BD136635 and BD136636).

Pollen-specific promoter: A gene sequence that is primarily expressed in pollen relative to the other cells of the plant. Includes any pollen-specific gene whose malfunction or functional deletion results in male-sterility. Examples include, but are not limited to: LAT52, LAT56, and LAT59 from tomato (GenBank Accession Nos. BG642507, X56487 and X56488), PS1 (GenBank Accession No. Z16402), and pollen specific gene from corn (GenBank Accession No. BD136635 and BD136636).

Promoter: An array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements that can be located as much as several thousand base pairs from the start site of transcription. Both constitutive and inducible promoters are included (Bitter et al., *Meth. Enzymol.* 153:516-44, 1987).

Specific, non-limiting examples of promoters that can be used to practice the disclosed methods include, but are not limited to, a floral-specific promoter, constitutive promoters, as well as inducible promoters for example a heat shock promoter, a glucocorticoid promoter, and a chemically inducible promoter. Promoters produced by recombinant DNA or synthetic techniques may also be used. A polynucleotide encoding a protein can be inserted into an expression vector that contains a promoter sequence that facilitates the efficient transcription of the inserted genetic sequence of the host. In one example, an expression vector contains an origin of replication, a promoter, as well as specific nucleic acid sequences that allow phenotypic selection of the transformed cells.

Recombinant: A recombinant nucleic acid is one that has a sequence that is not naturally occurring or has a sequence that is made by an artificial combination of two otherwise separated segments of sequence. This artificial combination can be accomplished, for example, by chemical synthesis or by the artificial manipulation of isolated segments of nucleic acids, e.g., by genetic engineering techniques. Similarly, a recombinant protein is one encoded for by a recombinant nucleic acid molecule.

Recombinase: A protein which catalyses recombination of recombining sites (reviewed in Kilby et al., *TIG*, 9:413-21, 1993; Landy, *Curr. Opin. Genet. Devel.*, 3:699-707, 1993; Argos et al., *EMBO J.*, 5:433-40, 1986). Non-limiting examples of recombinases include CRE, FLP, Tn3 recombinase, transposon gamma/delta, and transposon manner.

The cre and Flp proteins belong to the lambda/integrase family of DNA recombinases. The cre and Flp recombinases are similar in the types of reactions they carry out, the structure of their target sites, and their mechanism of recombination (Jayaram, *TIBS*, 19:78-82, 1994; Lee et al., *J. Biol. Chem.* 270:4042-52, 1995). For instance, the recombination event is independent of replication and exogenous energy sources such as ATP, and functions on both supercoiled and linear DNA templates.

Recombinases exert their effects by promoting recombination between two of their recombining sites. In the case of cre, the recombining site is a Lox site (see U.S. Pat. No. 4,959,317 to Sauer), and in the case of Flp the recombining site is a Frt site. Similar sites are found in transposon gamma/delta, TN3, and transposon mariner. These recombining sites include inverted palindromes separated by an asymmetric sequence (Mack et al., *Nuc. Acids Res.*, 20:4451-5, 1992; Hoess et al., *Nuc. Acids Res.* 14:2287-300, 1986; Kilby et al., *TIG*, 9:413-21, 1993). Recombination between target sites arranged in parallel (so-called "direct repeats") on the same linear DNA molecule results in excision of the intervening DNA sequence as a circular molecule. Recombination between direct repeats on a circular DNA molecule excises the intervening DNA and generates two circular molecules. The cre/Lox and flp/frt recombination systems have been used for a wide array of purposes such as site-specific integration into plant, insect, bacterial, yeast and mammalian chromosomes has been reported (Sauer et al., *Proc. Natl. Acad. Sci. USA*, 85:5166-70, 1988). Positive and negative strategies for selecting or screening recombinants are known (Sauer et al., *J. Mol. Biol.*, 223:911-28, 1992).

Recombining site: A nucleic acid sequence that includes inverted palindromes separated by an asymmetric sequence (such as a transgene) at which a site-specific recombination reaction can occur. Examples include, but are not limited to, Lox, Frt (consists of two inverted 13-base-pair (bp) repeats and an 8-bp spacer that together comprise the minimal Frt site, plus an additional 13-bp repeat which may augment reactivity of the minimal substrate, e.g. see U.S. Pat. No. 5,654,182), TN3, mariner, and a gamma/delta transposon.

Selectable marker: A nucleic acid sequence that confers a selectable phenotype, such as in plant cells, that facilitates identification of cells containing the nucleic acid sequence. Transgenic plants expressing a selectable marker can be screened for transmission of the gene(s) of interest. Examples include, but are not limited to: genes that confer resistance to toxic chemicals (e.g. ampicillin, spectinomycin, streptomycin, kanamycin, geneticin, hygromycin, glyphosate or tetracycline resistance, as well as bar and pat genes which confer herbicide resistance), complement a nutritional deficiency (e.g., uracil, histidine, leucine), or impart a visually distinguishing characteristic (e.g., color changes or fluorescence, such as β-gal).

Tapetum-specific gene: A gene sequence that is primarily expressed in the tapetum relative to the other tissues of the plant. Includes any tapetum cell-specific gene whose malfunction results in male-sterility. Examples include, but are not limited to: TA29 and TA13 (Goldberg, *Science* 240:1460-7, 1988), pca55 (WO92/13956), pE1 and pT72 (WO92/13957), Bcp1 from *Brassica* and *Arabidopsis* (GenBank Accession Nos. X68209 and X68211), A9 from *Brassicaceae* (GenBank Accession No. A26204), and TAZ1, a tapetum-specific zinc finger gene from *petunia* (GenBank Accession No. AB063169).

Tapetum-specific promoter: A DNA sequence that directs a higher level of transcription of an associated gene in tapetal tissue relative to the other tissues of the plant. Tapetum is nutritive tissue required for pollen development. Examples include, but are not limited to the promoters associated with the genes listed under tapetum-specific genes.

Transduced and transformed: A virus or vector "transduces" or "transfects" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule can be introduced into such a cell. Examples include, but are not limited to, transfection with viral vectors, transformation with plasmid vectors, electroporation (Fromm et al., *Proc. Natl. Acad. Sci. USA*. 82:5824-8., 1985; Fromm et al., *Nature* 319:791-3, 1986), lipofection (Felgner et al., *Proc. Natl. Acad. Sci USA* 84:7413, 1987), microinjection (Mueller et al., *Cell* 15:579, 1978), *Agrobacterium*-mediated transfer (Fraley et al., Proc. Natl. Acad. Sci. U S A. 80:4803-7, 1983), direct DNA uptake, and microprojectile bombardment (Klein et al., Nature 327:70, 1987).

Transgene: An exogenous nucleic acid sequence. In one example, a transgene is a gene sequence, for example a sequence that encodes a cytotoxic polypeptide. In yet another example, the transgene is an antisense nucleotide, wherein expression of the antisense nucleotide inhibits expression of a target nucleic acid sequence. A transgene can contain native regulatory sequences operably linked to the transgene (e.g. the wild-type promoter, found operably linked to the gene in a wild-type cell). Alternatively, a heterologous promoter can be operably linked to the transgene.

Transgenic Cell: Transformed cells that contain a transgene, which may or may not be native to the cell.

Vector: A nucleic acid molecule as introduced into a cell, thereby producing a transformed cell. A vector can include nucleic acid sequences that permit it to replicate in the host cell, such as an origin of replication. Examples include, but are not limited to a plasmid, cosmid, bacteriophage, or virus that carries exogenous DNA into a cell. A vector can also include one or more cytotoxic genes, antisense molecules, and/or selectable marker genes and other genetic elements known in the art. A vector can transduce, transform or infect a cell, thereby causing the cell to express the nucleic acids and/or proteins encoded by the vector. A vector optionally includes materials to aid in achieving entry of the nucleic acid into the cell, such as a, liposome, protein coating or the like.

Disclosed herein are methods for producing a perennial plant having decreased transgene escape, as well as perennial plants produced by such methods, such as a male-sterile perennial plant, and seeds produced by the plants. In one example, the method includes contacting a perennial plant with a vector, wherein the vector includes a cytotoxin operably linked to a floral-specific promoter. Expression of this vector results in the production of sterile progeny, such as a male or female sterile plant, or even total gametic sterility, thereby producing a producing a perennial plant having decreased transgene escape. For example, the vector can be transfected into cells of the plant. Examples of plants that can be used include, but are not limited to, turfgrass, roses, trees and grapes. In one example, the method results in a decrease in the production of viable pollen produced by the sterile plant. For example, the amount of viable pollen produced is less than 0.1%, for example less than 0.01%, for example less than 0.001%, as compared to a wild-type perennial plant of a same variety as the perennial plant having decreased transgene escape. The vector can be stably integrated into the genome of the plant.

The perennial plant having decreased transgene escape can have one or more desirable traits, such as two or more desirable traits, such as resistance to insects and other pests and disease-causing agents; tolerances to herbicides; enhanced stability, yield, or shelf-life; environmental tolerances; and nutritional enhancements. The desirable traits can be linked to the gene which results in decreased transgene escape. In one example, the desired trait is due to the presence of a transgene(s) in the plant. In another or additional example, the desired trait is obtained through convention breeding. In one example, decreased transgene escape is maintained through vegetative propagation.

Also disclosed are methods for producing a sterile perennial plant, as well as perennial plants produced by such methods, such as a male-sterile and/or female sterile perennial plant, and seeds produced by the plants. In one example, the method includes crossing a first fertile plant having one or more desirable traits, such as two or more desirable traits, with second fertile plant. The second plant can also have one or more desirable traits. The first fertile plant includes a vector, wherein the vector includes floral-specific promoter operably linked to a blocking sequence, such as a selectable marker, and the blocking sequence is flanked by recombining site sequences. In addition, the vector includes a cytotoxic sequence, which is downstream to the promoter and the blocking sequence, and is in a position such that its expression is activated by the floral-specific promoter in the presence of a recombinase, which results in recombination at the recombining site sequences and removal of the blocking sequence. The second fertile plant includes another vector which includes a promoter operably linked to a recombinase. The promoter can be a constitutive promoter, or an inducible promoter. If an inducible promoter is used, the second fertile plant is contacted with an inducing agent, before, during, or after crossing the first and second fertile plant. The inducing agent activates the inducible promoter, thereby permitting recombinase expression. If a constitutive promoter is used, the promoter will drive recombinase expression in the absence of an inducing agent. The expressed recombinase protein interacts with the recombining sites of the other vector, resulting in recombination, removal of the blocking sequence such that the floral-specific promoter is now operably linked to the cytotoxin, thereby driving expression of the cytotoxin in floral-specific tissues. The resulting progeny of such a cross are sterile. In one example, the vector included in the second fertile plant also includes a promoter operably linked to a blocking sequence. The vector can be stably integrated into the genome of the plant.

In an alternative example, instead of using two vectors, all of the elements are placed on a single vector, which is transfected into plants or plant cells. The first and/or second plant can include one or more, such as two or more desirable traits. The first or the second fertile plant includes a vector. The vector includes a floral-specific promoter operably linked to a blocking sequence, such as a selectable marker, wherein the blocking sequence is flanked by a recombining site sequence, a cytotoxic sequence downstream of the blocking sequence such that the cytotoxic sequence is operably linked to the promoter upon recombination, and a promoter (such as a constitutive or inducible promoter) operably linked to a recombines. If an inducible promoter is used, the plant transfected with the vector is contacted with an inducing agent, before, during, or after crossing the plants. The inducing agent, or constitutively active promoter, promotes recombinase expression. The expressed recombinase protein interacts with the recombining sites, resulting in recombination, removal of the blocking sequence such that the floral-specific promoter is now operably linked to the cytotoxin, thereby driving expression of the cytotoxin. The resulting progeny of such a cross are sterile. The vector can be stably integrated into the genome of the transfected plant.

Examples of site-specific recombination systems which can be used to practice the methods disclosed herein include the FLP/FRT system and the CRE/LOX system. However, one skilled in the art will understand that other systems can also be employed.

Any floral-specific promoter can be used to practice the disclosed methods, including variants thereof that are functionally equivalent and confer gene express in or predominantly in floral tissues. Particular examples include, but are not limited to: tapetum-specific promoters, such as a rice tapetum specific promoter, anther-specific promoters, pollen-specific promoters, ovule-specific promoters, megasporocyte-specific promoters, megasporangium-specific promoters, integument-specific promoters, stigma-specific promoters, and style-specific promoters. In one example, floral-specific promoters include an embryo-specific promoter or a late embryo-specific promoter, such as the late embryo specific promoter of DNH1 or the HVA1 promoter; the GLB1 promoter from corn, and any of Zein promoter (Z27).

Cytotoxin molecules include traditional cytotoxins such as barnase, as well as antisense molecules, such as floral-specific gene antisense sequences, that decrease or inhibit the development of floral structures, thereby leading to sterility of the plant.

Examples of blocking sequences that can be used, include, but are not limited to, non-coding DNA sequences, and a selectable marker sequence. Any selectable marker can be used. Particular examples include, but are not limited to: genes that confer resistance to toxic chemicals such as the bar and pat genes which confer herbicide resistance, and those that impart a visually distinguishing characteristic, such as a color change. In addition, any cytotoxic sequence can be used to practice the methods disclosed herein, as long as the gene interferes with floral development, such as pollen or tapetal development, thereby rendering the plant sterile. Particular examples include, but are not limited to ribonucleases, such as barnase, as well as antisense sequences, such as a tapetum-specific antisense gene sequence.

Any constitutive or inducible promoter can be used. Examples of inducible promoters that can be used to practice the methods disclosed herein include, but are not limited to: heat shock promoters, glucocorticoid promoters, transcriptionally regulated promoters, chemically inducible promoters, and light activated promotes. Promoters regulated by heat shock, such as the promoter associated with the gene encoding the 70-kDa heat shock protein, increase expression several-fold after exposure to elevated temperatures. The heat shock promoter can be used as an environmentally inducible promoter for controlling transcription of a recombinase, such as FLP. Glucocorticoid promoters include a gene encoding glucocorticoid receptor protein (GR) which in the presence of a steroid hormone forms a complex with the hormone. This complex binds to a short nucleotide sequence (26 bp) named the glucocorticoid response element (GRE), and this binding activates the expression of linked genes. The light inducible system is exemplified by promoters that drive expression of various photosynthetic genes, such as some of the SSU, CAB, and PEP carboxylase promoters.

In contrast to inducible promoters, constitutive promoters function under most environmental conditions. Many different constitutive promoters can be utilized with respect to the methods of this disclosure. Exemplary constitutive promoters include, but are not limited to, promoters from plant viruses such as the 35S promoter from CaMV (Odell et al., *Nature* 313:810-2, 1985; U.S. Pat. No. 5,858,742 to Fraley et al.); promoters from such plant genes as rice actin (McElroy et al., *Plant Cell* 2:163-71, 1990); ubiquitin (Christensen et al., *Plant Mol. Biol.* 12: 619-32, 1989); pEMU (Last et al., *Theor. Appl. Genet.* 81:581-8, 1991); MAS (Velten et al., *EMBO J.* 3:2723-30, 1984) and maize H3 histone (Lepetit et al., *Mol. Gen. Genet.* 231:276-85, 1992) and Atanassova et al., *Plant J.* 2:291-300, 1992); and the ALS promoter, a XbaI/NcoI fragment 5' to the *Brassica napus* ALS3 structural gene or a nucleotide sequence with substantial sequence similarity (PCT Application No. WO 96/30530). A particular example is a maize ubiquitin gene promoter.

EXAMPLE 1

Expression of Antisense rts or Barnase in Creeping Bentgrass Results in Male Sterility This example describes methods used to develop transgenic male sterile turfgrasses. Similar methods can be used to produce other transgenic male sterile perennials. The male sterile plants produced prevent or decrease escape of a transgene. Briefly, turfgrass cells were transformed with DNA sequences that cause herbicide resistance and male sterility.

Generation of Plasmids

Figure 1B:
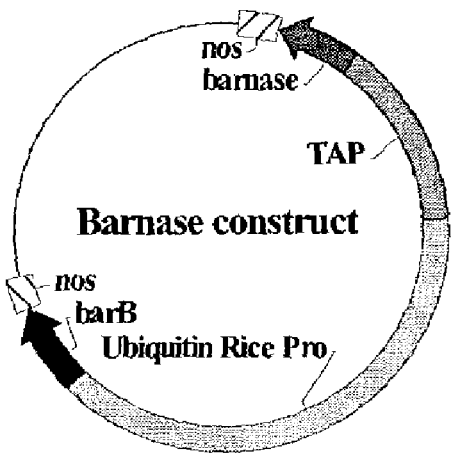

To induce male-sterility in creeping bentgrass (*Agrostis palustris* Huds.) (Penn-A-4, Turf-Seed, Inc., Hubbard, Oreg.), constructs containing an antisense rice tapetum-specific gene (rts) gene (FIG. 1A), or a ribonuclease gene from *Bacillus amyloliquefaciens* called barnase (FIG. 1B), were introduced separately into creeping bentgrass using *Agrobacterium tumefaciens*-mediated transformation as described below. A set of pSB11-based *Agrobacterium* binary vectors for turfgrass transformation with the antisense of a rts (sense sequence shown in SEQ ID NO: 1) and a ribonuclease gene from *Bacillus amyloliquefaciens*, called barnase, both under the control of a rice tapetum-specific promoter TAP (original driving rts gene, SEQ ID NO: 2). To synthesize the antisense rts- and barnase-expression vectors containing the herbicide-resistant bar gene as a selectable marker, the HindIII-BamHI fragment (corn ubiquitin promoter) from pAHC27 was cloned into respective sites of the pSBbarB to replace the original 35S promoter, generating pSB-UbibarB. The antisense rts gene and barnase gene expression cassettes were then be added to obtain the final male sterility-inducing vectors shown in FIGS. 1A and B. To generate the antisense rts expression vector, the PvuII fragment from pTAP (anti-sense) including the tapetum-specific promoter TAP driving antisense rts gene was ligated into the flushed HindIII site of pSB-UbibarB. To generate the barnase gene expression vector, a 0.52 kb barnase coding sequence from pMT416 was amplified by PCR using primers: 5'-CACAGGAAACAGGATCCGCGG-3' (SEQ ID NO: 3) and 5' CGC GAGCTCGCCGGAAAGTGAAATTGACC-3' (SEQ ID NO: 4) (underlined is the SstI restriction site). The amplified PCR product was digested with SstI and cloned into pTAP/gus after gus coding fragment being removed by SmaI/SacI digestion, generating pTAP/barnase. The tapetum-specific promoter TAP driving barnase gene was released from pTAP/barnase as a PvuII fragment and ligated into the flushed HindIII site of pSB-UbibarB. The vectors are designated as p115 for the antisense rts gene (FIG. 1A) and p127 for the barnase gene (FIG. 1B).

Because the barnase gene and the antisense rts gene are under the control of the rice tapetum-specific promoter TAP, the antisense rts gene and barnase gene are expressed in tapetal cells and microspores of the transgenic turfgrass.

Transformation of Plants

Several systems can be used to transform plant cells. The methods disclosed herein are not limited to any particular transformation method. Methods that can be used to transform turfgrass species (such as creeping bentgrass, tall fescue, perennial rye grass, Bermuda grass, and Kentucky blue grass) include, but are not limited to, biolistics, *Agrobacterium*, and whisker-mediated transformation. A strain similar to the *Agrobacterium* superbinary system was used with a tissue culture approach for selection of bar gene expression in transformed *Agrostis palustris* (cvs Penn A4) cells. The plasmids with gene constructs of interest were introduced into *Agrobacterium tumefaciens* strains LBA4404 (containing co-integrative vector pSB111) by triparental mating or electroporation (Hiei et al., *Plant J.* 6:271-82, 1994). The two plasmids co-integrate by homologous recombination in *Agrobacterium tumefaciens* cells (Komari et al., *Plant J.* 10:165-174, 1996).

Mature seeds of creeping bentgrass (cultivars Penn A4) were surface-sterilized and plated on callus induction media (modified MMSG or MSA2D media). The plates were kept in the dark at room temperature (RT) for 3-6 weeks. The proliferating calli were selected and transferred to new maintenance medium on a regular basis. Only callus that is friable and regenerable was used for transformation. The chosen callus was transferred to fresh medium prior to co-cultivation with *Agrobacterium* to promote active cell division. This callus was used for transformation within a week after transferring to new plates.

*Agrobacterium tumefaciens* was induced with acetosyringone as follows. *Agrobacterium tumefaciens* LBA4404, harboring male sterility vectors were streaked from a glycerol stock and grown at 28° C. on plates containing AB medium, supplemented with 10 μg/ml tetracycline and 50 μg/ml spectinomycin. After three to six days, the cells were scraped from the plate and suspended in *Agrobacterium* growth medium containing 100 μM acetosyringone, and grown to an $OD_{660}$ of about 0.1-0.5. The bacterial suspension was incubated at 25° C. in the dark with shaking for 3.5 hours before using it for co-cultivation.

Friable callus (0.001 mg-100 g) was mixed with the pre-induced *Agrobacterium* suspension and incubated at room temperature in the dark for 1.5 hours. The contents were poured into a sterile Buchner-funnel containing a sterile Whatman filter paper. Mild vacuum was applied to drain the excess *Agrobacterium* suspension. The filter was moved to a plate containing maintenance medium supplemented with 100 μM acetosyringone, and the plate stored in the dark at room temperature for three days. Subsequent to the three day co-cultivation, the co-cultivated calli were rinsed with 250 mg/ml cefotaxime to suppress bacterial growth, and the calli placed on agar plates containing maintenance medium which included 15 mg/L PPT (phosphinothricine, for bar selection) and 250 μg/ml cefotaxime. The calli were kept in the dark at RT for 6-8 weeks and checked periodically for proliferation of the calli on the 15 mg/L PPT. Subsequently, the PPT-resistant calli were placed on regeneration medium containing PPT and cefotaxime. The proliferating calli were first moved to Regeneration Medium I containing cefotaxime (Research Products International Corp.) and PPT (Duchefa Biochemie, B.V.). The tiny plants were separated and transferred to deep petri plates containing Regeneration Medium II to promote root growth. PPT and cefotaxime were included in the medium to respectively maintain selection pressure and kill any remaining *Agrobacterium* cells. After 2-3 weeks, or when the plants were 1.5-2 cm tall, they were moved to plant-cons containing MSO II without antibiotics. When the plants are about 10 cm tall and develop extensive root systems, they were transferred to soil and grown for 3-4 weeks with 12 hours light/day. The plants were then transferred to 6-inch pots in the greenhouse, where the temperature is maintained between 21-25° C. Supplemental lighting can be added to increase timing of light exposure for flowering.

Generation T0 Male Sterile Transformants

The transgenic plants were vegetatively propagated and increased. The T0 plants produce seeds by backcrossing to the recipient variety and outcrossing to other cultivars for transmission of the transgenic traits.

Transformants were screened for glufosinate resistance by 'paint assays' to leaves and subsequently analyzed by standard molecular procedures (PCR and Southern blotting) to characterize the insertion events in the regenerating T0 plants and their stability in subsequent generations. The plants were sprayed with 0-100% v/v of liberty or finale (Aventis Corp.) and shown to be resistant to the herbicide (FIG. 2). Southern analysis using the bar gene and/or barnase as probes revealed transgene insertion in the male-sterile plants. Therefore, stable transformation of creeping bentgrass was achieved, as evidenced by the resistance of the plants to herbicide (due to the presence of the bar gene) and the male sterility due to the presence of the male sterile constructs.

Developmental and Phenotypic Analysis of Pollen Development and Viability

The herbicide-resistant male sterile T0plants had normal vegetative growth and morphology in comparison to non-transgenic tissue culture regenerated plants. As described above, transformation of herbicide tolerant creeping bentgrass was achieved. All transgenic plants were linked to one or the other male sterility construct (p115 or p127, FIGS. 1A and 1B) as shown by macrophotography and light microscopy.

Figure 3A:
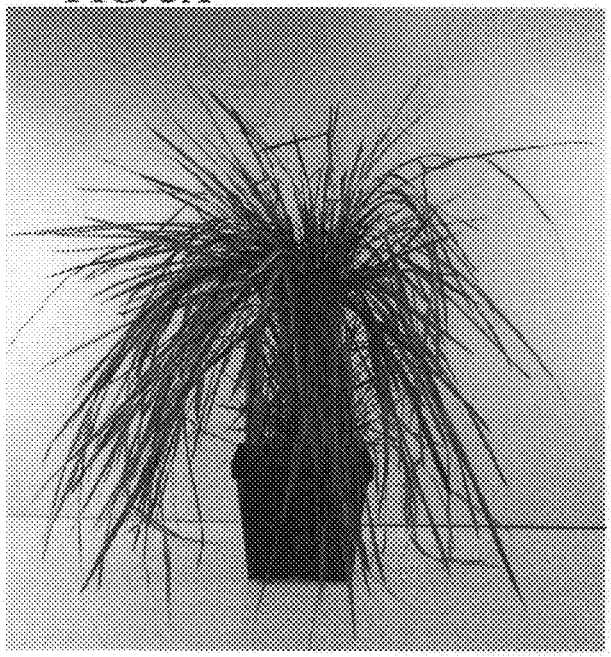
FIGS. 3A-C are digital images demonstrating that a flowering herbicide resistant male sterile T0 plant transfected with P127 vector has (A) normal growth and morphology in comparison to non-transgenic plants except that (B) the anthers are shrunken and (C) the pollen is aborted prior to the starch filling stage.
Figure 3B:
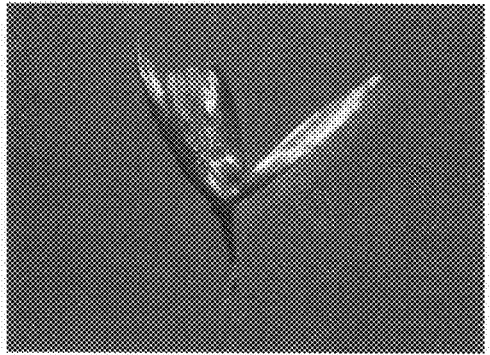
Figure 3C:
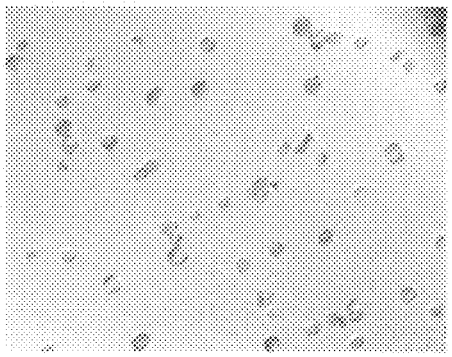

In addition, flowering herbicide resistant male sterile T0plants had normal vegetative growth and morphology in comparison to non-transgenic tissue culture regenerated plants (FIG. 3A), except the anthers were shrunken (FIG. 3B) and the pollen was aborted prior to the starch filling stage as indicted by IKI2 (iodine) staining (FIG. 3C). Pollen was obtained from transfected and control plants, and the viability determined by staining with iodine (IKI2) and examination by microscopy, using methods known to those skilled in the art (for example, see Johansen, D. A., 1940. Plant Microtechnique. MaGraw-Hill. New York). Wild-type pollen was heavily stained with IKI2, indicating that the pollen is filled with starch and viable. Pollen viability for wild-type plants was between 30-85%. In contrast, transgenic plants (plants transfected with P127 or p 115, FIGS. 1A and 1B) had no visible IKI2 staining, indicating that the pollen is not filled with starch, and thus not viable (FIG. 3C). In addition, fewer pollen grains were observed in the male sterile plants. Out of 174 p115 transformed plants, 79 plants flowered, and 40 of them were sterile. Out of 47 p127 transformed plants, 11 flowered and 10 of these were sterile.

Pollen fertility was determined using several methods, including in vitro pollen germination analysis, in vivo pollen tube studies, and a fertility test to nontransgenic varieties analyzed for glufosinate resistance.

EXAMPLE 2

Generation of T1 Plants Yields Male Sterile Plants which Segregate with the Bar Gene To generate T1 plants, the sterile male T0 plants generated above were crossed with fertile wild-type creeping bentgrass. The bar gene segregated in Mendellian ratios of approximately 1:1. One-half of the T1 plants were also male sterile and one-half were male fertile as evidenced by the absence of starch accumulation in the pollen in about 50% of the T1 plants. Wild-type T1 plants exhibited 70-95% pollen viability, while male sterile T1 plants exhibited >0.001% (p115) or 0.1-0.01% (p127) viability. Flower development was observed in male sterile plants in comparison to wild type plants by light microscopy. The flower and the anthers in T1 male sterile plants appear normal with respect to the wild type except that they do not undergo the starch filling phase of pollen maturation. The PCR results on the T1 male sterile plants demonstrate the presence of the introduced constructs encoding the bar gene and the male sterility genes.

The male sterile plant phenotype segregated with the bar gene as evidenced by herbicide resistance and the expression of the male sterility genes. Since the bar gene segregated with the tapetum-specific promoter driving male sterile expression as a dominant Mendellian characteristic, overseeding can be easily used by consumers with proper management. Seed producers can plant alternate rows of male sterile and male fertile stocks.

Breeding through Backcrossing to Wild-type Female and Analysis on Hemizygous T2 Transformants The resulting progeny from backcrossing T1 plants will be hemizygous for the bar selectable marker as well as the male sterile phenotype. Molecular analysis (such as PCR and Southern hybridization) can be conducted to confirm ability for transmission of the male sterile trait.

EXAMPLE 3

Site-specific Recombination to Decrease Transgene Escape in Perennials

Disclosed is a method for using site-specific recombination to generate male sterile offspring from fertile, transgenic parents. The resulting second-generation offspring are male sterile and will produce male sterile seed when fertilized by a male fertile donor plant. In addition, this technology allows the capability of deleting unwanted DNA sequences (such as antibiotic resistance markers) from transgenic plants. This example describes methods using the FLP/FRT recombinase system. However, one skilled in the art will understand that alternative recombinase systems can be used, such as the CRE/LOX or RS systems.

Site-specific recombinases are enzymes that recognize specific DNA sequences, and in the presence of two such recombination sites they catalyze the recombination of DNA strands (Ow and Medberry, *Crit. Rev. Plant Sci.* 14, 239-261, 1995). In the FLP/FRT system, for example, FLP can catalyze excision/integration or inversion of a DNA fragment according to the orientation of the two FRT sites. Recombination between directly oriented sites leads to excision of the DNA between them, whereas recombination between inverted target sites causes inversion of the DNA between them. Some site-specific recombination systems do not require additional factors for their function and are capable of functioning accurately and efficiently in various heterologous organisms. For example, FLP/FRT from the 2 μm plasmid of *Saccharomyces cerevisiae* (Broach et al., *Cell*, 29, 227-234, 1982) and Cre/lox from *E. coli* phage P1 (Austin et al., *Cell*, 25, 729-736, 1981) efficiently catalyze DNA recombination in dicot and monocot plant cells (for example see Bar et al., *Theor. Appl. Genet.* 93, 407-413, 1996; Bayler et al., *Plant Mol. Biol.* 18, 353-361, 1992; Dale and Ow, *Proc. Natl. Acad. Sci. USA*, 88, 10558-10562, 1991; Kilby et al., *Plant J.* 8, 637-652, 1995; Lloyd and Davis, *Mol. Gen. Genet.* 242, 653-657, 1994; Lyznik et al., *Nucleic. Acids Res.* 21, 969-975, 1993; Lyznik et al., *Nucleic. Acids Res.* 24, 3784-3789, 1996; Odell et al., *Mol. Gen. Genet.* 223, 369-378, 1990; Russel et al., *Mol. Gen. Genet.* 234, 49-59, 1992; Sonti et al., *Plant Mol. Biol.* 28, 1127-1132, 1995; Srivastava et al., *Proc. Natl. Acad. Sci. USA*, 96, 11117-11121, 1999).

Plant Expression Cassettes for Site-specific Recombination

Figure 4:
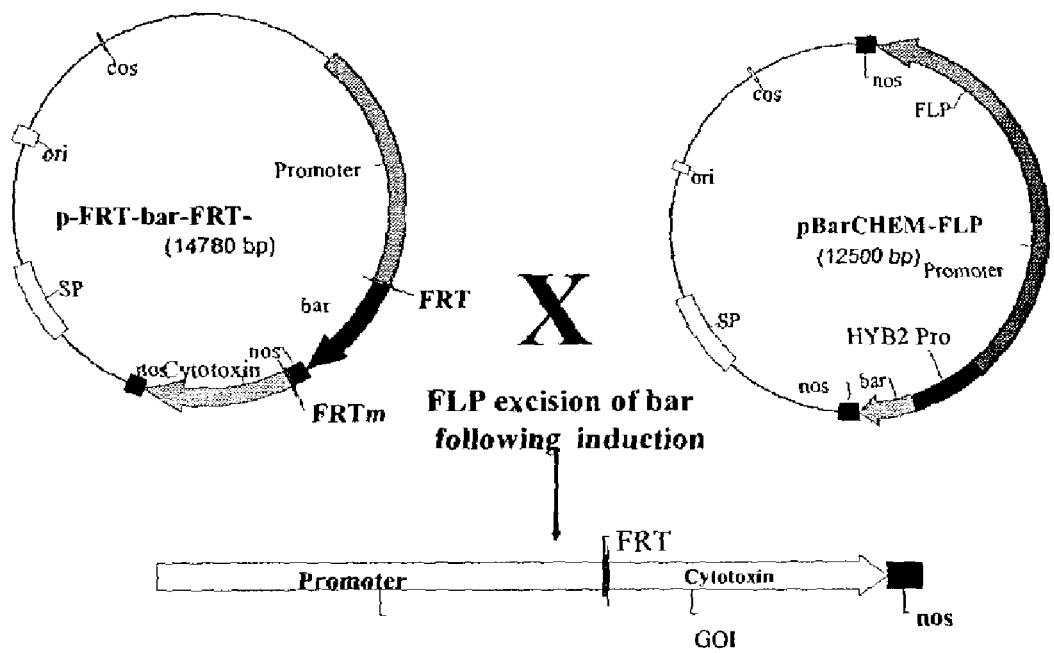
FIG. 4 is a schematic diagram of plasmids that can be used in an Flp/Frt recombinase system. The FRT plasmid includes a promoter, FRT and FRTm sequences that flank a blocking sequence (such as the bar selectable marker) followed by a cytotoxic sequence. The FLP plasmid includes a selectable marker (such as bar) and a promoter that drives expression of FLP. Expression of FLP causes recombination at the FRT sites, excising the blocking sequence in the FRT plasmid, allowing the promoter to drive expression of the cytotoxin sequence.

Two pSB11-based *Agrobacterium* binary vectors for plant transformation can be generated as follows (FIG. 4). The first, the vector containing FRT sites, includes a floral-specific promoter, the FRT and FRTm sequences which flank a blocking DNA fragment (such as a selectable marker), followed by a cytotoxic gene (such as a barnase sequences or an antisense sequence). The cytotoxic gene is therefore separated from the promoter by the blocking DNA fragment bracketed by recombination targeting sequences. The second vector, the FLP recombinase vector, includes an FLP recombinase driven by a promoter, such as a constitutively active promoter (for example the rice ubiquitin promoter, rice Actin 1, corn ubiquitin promoter, and the 35S CaMV promoter) or an inducible promoter. Examples of selectable markers include thee bar or pat genes which can be driven by a Ubiquitin corn promoter (Ubi-c) with an nos 3" termination signal. Examples of inducible promoters include, but are not limited to, those responsive to environmental stimuli (for example see Ainley and Key, *Plant Mol. Biol.* 14:949-67, 1990; Kyozuka et al., *Plant Physiol.* 102:991-1000, 1993; Lyznik et al., *Plant J.* 8:177-86, 1995) or synthetic chemicals (for example see Ayoma and Chua, *Plant J.* 11, 605-612, 1997; Caddick et al., *Nat. Biotechnol.* 16:177-80, 1998; Gatz, *Annu. Rev. Plant Physiol. Plant Mol. Biol.* 48, 89-108, 1997; Gatz and Lenk, *Trends Plant Sci.* 3, 322-328, 1998; Mett et al., *Proc. Natl. Acad. Sci. USA.* 90:4567-71, 1993; Picket and Poppy, *Trends Plant Sci.* 6, 137-139, 2001; Ward et al., *Plant Mol. Biol.* 22, 361-366, 1993; Zuo et al., *Plant J.* 24, 265-273, 2000; Zuo et al., *Nat. Biotechnol.* 19, 157-161, 2001). Ideally, an inducible promoter is highly inducible by agents or signals that can readily penetrate the seed or other plants parts, is non-toxic, inexpensive, environmentally acceptable, and its expression essentially 'non-leaky'. One skilled in the art will understand that other recombinase systems can be used. For example, Cre can be substituted for FLP and Lox can be substituted for FRT.

To synthesize this portion of the FRT vector containing the herbicide-resistant bar gene as a selectable marker, the HindIII-BamHI fragment (corn ubiquitin promoter) from pAHC27 is cloned into respective sites of the pSBbarB to replace the original 35S promoter, giving rise to pSB-UbibarB. The 34 bp FRT sequence is blunt end ligated to the 5' end of the pSB-UbibarB and the FRTm sequence added to the 3' end. To synthesize the FLP-expression vector, the modified FLP gene is released as a SalI (flushed with DNA Polymerase I, Klenow fragment, Biolabs)-SacI fragment from the plasmid JFLO (Luo et al., *Plant J.* 23:423-430, 2000) and ligated into the BamHI (flushed with DNA Polymerase I, Klenow fragment, Biolabs)-SacI sites of the plasmid pEH30 to replace the original gusA gene. The modified FLP gene includes a plant consensus sequence around the ATG codon. The HindIII-EcoRI fragment containing the FLP gene driven by the inducible promoter is released, flushed with DNA Polymerase I, Klenow fragment and ligated into the vector described above giving rise to the final construct.

FLP expression in the presence of the inducing agent causes excision of the FRT flanked sequences juxtaposing the promoter in the FRT vector and the cytotoxic gene renders the resultant plant sterile.

Methods for Decreasing Transgene Escape

Each plasmid is transfected into a different plant (for example using *Agrobacterium tumefaciens* LBA4404 produced by triparental mating or electroporation as described in Example 1 to infect plant cells which are then selected by resistance to the selectable marker bar), and the resulting T0 fertile herbicide-resistant transgenic plants are selfed and/or crossed with fertile wild type plants. The plants containing the FLP vector are also either selfed and/or crossed with fertile wild type plants. The resulting T1 plants segregate according to Mendiallian ratios. The homozygous T1 plants are herbicide resistant and are crossed as parents. The progeny can be exposed to the inducer prior to, during or after crossing, to drive expression of the recombinase. The resulting progeny will receive both promoters, such that when recombinase expression is induced in the progeny, the recombinase removes the FRT-flanked blocking DNA sequence (such as a selectable gene, or noncoding DNA), bringing together the promoter and the cytotoxic sequence. The expression of the cytotoxic sequences produces male sterile or sterile transgenic plants.

Linked Regulation

In order to avoid variation that may be introduced by crossing the FLP function in during the last pollination during seed production, the entire recombinase system can be designed to be in one expression cassette as shown in FIGS. 5-8. In this method, the recombinase (such as FLP recombinase) is under promoter (such as a chemical inducer as shown in FIG. 5) and operably linked to a cytotoxic gene, such as barnase. In one particular example, the promoter is a floral apex specific promoter, such that its expression would result in ablation of the entire infloresecence resulting in total infertility.

In addition, methods for elimination of invasive plants, by creating a bio-herbicide are disclosed which permit the ability to safely eliminate an invasive plant against a stable ecological background without effects on other plants. The promoter shown in FIG. 6 is an embryo specific promoter (Glb1) from maize, such that after induction the blocking sequence is removed, and permits expression of the cytotoxic gene through the Glb1 promoter. The seeds produced by such a transgenic plant are sterile. Induced transgenic seeds can be sown as a bioherbicide to control invasive plants and weeds without the use of chemicals.

Another variation shown in FIGS. 7 and 8 depicts a light inducible promoter, such that the recombinase is activated after the seed germinates, excising the blocking sequence, such that the pollen carries the cytotoxic sequence. In another example, the transmitted poll can kill the entire plant, in this case the cytotoxic gene could be any element which is systemic and lethal. The systemic portion can be directed by a movement protein (such as the TMV movement protein). The cytotoxic gene can be activated by an inducible promoter, such as a chemically inducible promoter. If this is an environmentally acceptable inducible promoter, only the pollinated plants of the specific species are eliminated when the promoter is activated.

We claim:

1. A method of producing a turfgrass having decreased transgene escape, comprising:
   contacting a turfgrass cell with a vector, wherein the vector comprises a cytotoxin-encoding sequence operably linked to a rice tapetum-specific promoter, thereby producing a transgenic plant cell; and
   growing the transgenic plant cell into a plant, thereby producing a turfgrass having decreased transgene escape.

2. The method of claim 1, wherein the method produces a female sterile plant.

3. The method of claim 1, wherein the method produces total gametic sterility.

4. The method of claim 1, wherein the method produces a male sterile plant.

5. The method of claim 1, wherein the cytotoxin is an antisense molecule.

6. The method of claim 5, wherein the antisense molecule is a tapetum-specific gene antisense sequence.

7. The method of claim 1, wherein the cytotoxin is barnase.

8. The method of claim 1, wherein the method decreases development of viable pollen.

9. The method of claim 8, wherein an amount of viable pollen produced is less than 0.1% as compared to a wild-type turfgrass of a same variety as the turfgrass having decreased transgene escape.

10. The method of claim 9, wherein an amount of viable pollen produced is less than 0.01% as compared to a wild-type turfgrass of a same variety as the turfgrass having decreased transgene escape.

11. The method of claim 1, wherein the turfgrass having decreased transgene escape comprises one or more desirable traits.

12. The method of claim 11, wherein the desirable traits are selected from the group consisting of herbicide resistance, drought tolerance, and disease resistance.

13. The method of claim 11, wherein the one or more desirable traits is linked to decreased transgene escape.

14. The method of claim 1, wherein decreased transgene escape is maintained through vegetative propagation.

15. A turfgrass plant produced by the method of claim 1.

16. A male-sterile turfgrass plant produced by the method of claim 1.

17. Seed of the plant of claim 15 or 16, wherein the seed is sterile.

18. The method of claim 1, wherein contacting the turfgrass cell comprises transforming the turfgrass cell with the vector.

19. The method of claim 1, wherein the turfgrass is creeping bentgrass.

20. The method of claim 1, wherein the rice tapetum-specific promoter comprises the nucleic acid sequence shown in SEQ ID NO: 2.

21. The method of claim 6, wherein the tapetum-specific gene antisense sequence comprises an antisense sequence corresponding to the sense nucleic acid sequence shown in SEQ ID NO: 1.

22. The method of claim 18, wherein transforming the turfgrass cell with the vector comprises introducing the vector into the turfgrass cell using *Agrobacterium tumefaciens*-mediated transformation.

23. The method of claim 22, wherein a callus generated from mature turfgrass seed comprises said turfgrass cell.

24. The method of claim 1, wherein the cytotoxin is RNase-T1, avidin, DAM methylase, or Diphtheria toxin.

* * * * *